United States Patent
Warner et al.

(10) Patent No.: US 6,458,793 B1
(45) Date of Patent: Oct. 1, 2002

(54) HETEROCYCLIC DERIVATIVES WHICH INHIBIT FACTOR XA

(75) Inventors: Peter Warner; Roger James; Thorsten Nowak, all of Macclesfield (GB)

(73) Assignee: Zeneca Limited, London (GB)

(*) Notice: Subject to any disclaimer, the term of this patent is extended or adjusted under 35 U.S.C. 154(b) by 0 days.

(21) Appl. No.: 09/463,625

(22) PCT Filed: Jul. 23, 1998

(86) PCT No.: PCT/GB98/02210

§ 371 (c)(1),
(2), (4) Date: Jan. 28, 2000

(87) PCT Pub. No.: WO99/06371

PCT Pub. Date: Feb. 11, 1999

(30) Foreign Application Priority Data

Jul. 29, 1997 (GB) .............................. 9715894

(51) Int. Cl.⁷ .................. C07D 401/14; C07D 401/12; A61K 31/455
(52) U.S. Cl. ............................ 514/253.13; 514/253.01; 514/332; 514/334; 544/364; 544/365; 546/255; 546/256; 546/257
(58) Field of Search ................. 514/253.13, 253.01, 514/332, 334; 544/364, 365; 546/255, 256, 257

(56) References Cited

U.S. PATENT DOCUMENTS 5,037,824 A * 8/1991 Takasugi et al. .......... 514/227.8
5,541,330 A * 7/1996 Wear et al. ................. 546/257

FOREIGN PATENT DOCUMENTS

WO 96/10022 A 4/1996
WO 97/28129 8/1997
WO 98/21188 A 5/1998

OTHER PUBLICATIONS

Zhu et al., Factor Xa Inhibitors: Recent Advances In Anticoagulant Agents, Ann. Reports Med. Chem., 35, pp. 83–102, 2000.*
Kawasaki et al. (PubMed Abstract—Nippon Yakurigaku Zasshi, 116(5):275–82, Nov. 2000).*
Sherman, (PubMed Abstract—Neurology, 51(3 Suppl): S56–8, Sep. 1998).*
Zurita et al., Chem. Abstract 122:155055, 1995.*
Lutz et al., Chem. Abstract 125:300774, 1996.*
Kunitada S et al: "Factor XA Inhibitors" Current Pharmaceutical Design, vol. 2, No. 5, Oct. 1996, pp. 531–542, XP002057653, see p. 539.

* cited by examiner

Primary Examiner—Deepak R. Rao
(74) Attorney, Agent, or Firm—Morgan, Lewis & Bockius LLP

(57) ABSTRACT

The invention relates to heterocyclic derivatives, or pharmaceutically-acceptable salts thereof, which possess antithrombotic and anticoagulant properties and more accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect, formula (I).

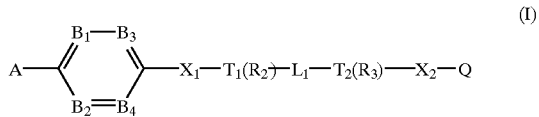

5 Claims, No Drawings

HETEROCYCLIC DERIVATIVES WHICH INHIBIT FACTOR XA

This application is the national phase of international application PCT/GB96/02210 filed Jul. 23, 1998 which designated the U.S.

The invention relates to heterocyclic derivatives, or pharmaceutically-acceptable salts thereof, which possess antithrombotic and anticoagulant properties and are accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by R. B. Wallis, *Current Opinion in Therapeutic Patents*, 1993, 1173–1179. Thus it is known that two proteins, one known as antistatin and the other known as tick anticoagulant protein (TAP), are specific Factor Xa inhibitors which possess antithrombotic properties in various animal models of thrombotic disease.

It is also known that certain non-peptide compounds possess Factor Xa inhibitory properties. Of the low molecular weight inhibitors mentioned in the review by R. B. Wallis, all possessed a strongly basic group such as amidinophenyl or amidinonaphthyl group.

We have now found that certain heterocyclic derivatives possess Factor Xa inhibitory activity. Many of the compounds of the present invention also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

The compounds of the present invention possess activity in the treatment or prevention of a variety of medical disorders where anticoagulant therapy is indicated, for example in the treatment or prevention of thrombotic conditions such as coronary artery and cerebro-vascular disease. Further examples of such medical disorders include various cardiovascular and cerebrovascular conditions such as myocardial infarction, the formation of atherosclerotic plaques, venous or arterial thrombosis, coagulation syndromes, vascular injury including reocclusion and restenosis following angioplasty and coronary artery bypass surgery, thrombus formation after the application of blood vessel operative techniques or after general surgery such as hip replacement surgery, the introduction of artificial heart valves or on the recirculation of blood, cerebral infarction, cerebral thrombosis, stroke, cerebral embolism, pulmonary embolism, ischaemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

Accordingly in one aspect the present invention provides compounds of the formula

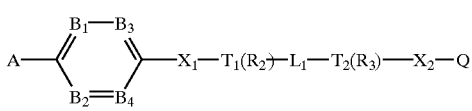

wherein:
A is an optionally substituted 5- or 6-membered monocyclic aromatic ring containing 1, 2 or 3 ring heteroatoms selected from oxygen, nitrogen and sulphur atoms;
$B_1$, $B_2$, $B_3$ and $B_4$ are independently CH or a nitrogen atom, wherein the ring formed from $B_1$, $B_2$, $B_3$ and $B_4$ may optionally be substituted; with the proviso that at least one of $B_1$, $B_2$, $B_3$ and $B_4$ is nitrogen;
$T_1$ is CH or N;
$T_2$ is CH or N;
with the proviso that at least one of $T_1$ and $T_2$ is N;
$X_1$ is SO, $SO_2$, $C(R_4)_2$ or CO when $T_1$ is CH or N; or in addition $X_1$ is O or S when $T_1$ is CH;
and wherein each $R_4$ is independently hydrogen or (1-4C) alkyl;
$L_1$ is (1-4C)alkylene or (1-3C)alkylenecarbonyl;
$R_2$ is hydrogen or (1-4C)alkyl;
$R_3$ is hydrogen or (1-4C)alkyl;
or $R_2$ and $R_3$ are joined to form a $C_{1-4}$alkylene or —$CH_2$CO— group; wherein the ring formed by $T_1$, $R_2$, $R_3$, $T_2$ and $L_1$ is optionally substituted;
$X_2$ is S(O), wherein y is one or two, $C(R^5)_2$ or CO; and each $R^5$ is hydrogen or (1-4C)alkyl;
Q is phenyl, naphthyl, phenyl(1-4C)alkyl, phenyl(2-4C) alkenyl, phenyl(2-4C)alkynyl or a heterocyclic moiety containing up to 4 ring heteroatoms selected from nitrogen, oxygen and sulphur and Q is optionally substituted;
and pharmaceutically acceptable salts thereof.

In this specification the term "alkyl" includes both straight and branched chain alkyl groups but references to individual alkyl groups such as "propyl" are specific for the straight chain version only. An analogous convention applies to other generic terms.

It is to be understood that certain heterocyclic derivatives of the present invention can exist in solvated as well as unsolvated forms such as, for example, hydrated forms. It is to be understood that the invention encompasses all such solvated forms which possess Factor Xa inhibitory activity.

It is further to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or by resolution of a racemic form.

Preferably A is a pyridyl, pyrimidinyl or pyridazinyl ring for example 4-pyridyl, 2-pyridyl, 4-pyridazinyl, 3-pyrimidinyl, 4-pyrimidinyl or 3-pyridyl. Of these 4-pyrimidinyl, 4-pyradazinyl and 4-pyridyl are most preferred.

In one aspect A is unsubstituted. In another aspect A is substituted by one, two or three atoms or groups selected from halo (for example fluoro, chloro or bromo), trifluoromethyl, cyano, amino, oxo, hydroxy, nitro, (1-4C) alkyl (for example methyl or ethyl). $C_{1-4}$alkoxy (for example methoxy or ethoxy), (1-4C)alkylamino (for example methylamino or ethylamino) or di-(1-4C)alkylamino (for example dimethylamino or diethylamino). For the avoidance of doubt substituents may also be on any heteroatom.

Preferably the ring formed by $B_1$, $B_2$, $B_3$ and $B_4$ is a pyridinediyl, wherein $B_1$, or $B_3$ is a nitrogen atom, pyrimidinediyl, wherein $B_1$ and $B_2$ or $B_3$ and $B_4$ are nitrogen atoms, pyridazinediyl, wherein $B_1$, $B_3$ and $B_4$ or $B_1$, $B_2$ and $B_3$ are nitrogen atoms. Of these pyridinediyl and pyrimidinediyl are preferred.

In one aspect the ring containing $B_1$, $B_2$, $B_3$ and $B_4$ is unsubstituted. In another aspect the ring containing $B_1$, $B_2$, $B_3$ and $B_4$ is substituted by one or two substituents selected from hydroxy, carboxy, (1-4C)alkoxycarbonyl or one of the following:

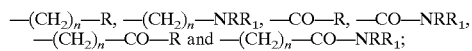

wherein:

n is 1 or 2;

R and $R_1$ are independently selected from hydrogen, (1-4C)alkyl, (2-4C)alkenyl, (2-4C)alkynyl, hydroxy(1-4C)alkyl, carboxy(1-4C)alkyl and (1-4C) alkoxycarbonyl-(1-4C)alkyl or where possible R and $R_1$ may together form a 5- or 6-membered optionally substituted heterocyclic ring which may include in addition to the nitrogen atom to which R and $R_1$ are attached 1 or 2 additional heteroatoms selected from nitrogen, oxygen and sulphur.

In a particular aspect the heterocyclic rings formed by R and $R_1$ are preferably selected from pyrrolidin-1-yl, imidazolin-1-yl, piperidin-1 yl, piperazin-1-yl, 4-morpholino and 4-thiomorpholino. In a particular aspect the heterocyclic ring formed by R and $R_1$ may be unsubstituted. In an alternative aspect the ring formed by R and $R_1$ is substituted by 1 or 2 substituents selected from oxo, hydroxy and carboxy.

In a particular aspect, when $T_1$ is CH or N, $X_1$ is CO, $SO_2$, or $CH_2$, when $T_1$ is CH. $X_1$ in addition is O or S. Preferably $X_1$ is CO.

$T_1$ is CH or N and $T_2$ is CH or N with the proviso that at least one of $T_1$ and $T_2$ is N. For the avoidance of doubt $T_1$ is directly attached to the groups $X_1$ and $L_1$ and $T_2$ is directly attached to the groups $L_1$ and $X_2$.

$L_1$ is $C_{1-4}$alkylene for example methylene, ethylene or propylene or is $C_{1-3}$alkylenecarbonyl for example methylenecarbonyl (—$CH_2CO$—).

In one aspect $R_2$ is hydrogen or $C_{1-4}$alkyl for example methyl or ethyl. In one aspect $R_3$ is hydrogen or $C_{1-4}$alkyl for example methyl or ethyl.

In a preferred aspect $R_2$ and $R_3$ are joined to form a $C_{1-4}$alkylene group, for example a methylene, ethylene or propylene group, or a methylenecarbonyl (—$CH_2CO$—) group.

In a particular aspect $R_2$ and $R_3$ are joined to form, together with $T_1$, $T_2$ and $L_1$, a heterocyclic ring wherein at least one of $T_1$ and $T_2$ is N. Examples of such heterocyclic rings are piperazine (wherein $T_1$ and $T_2$ are both N), piperidine (wherein either $T_1$ or $T_2$ is N and the other is CH) and pyrrolidine (wherein either $T_1$ or $T_2$ is N and other is CH).

In one aspect the heterocyclic ring formed by $T_1$, $T_2$, $L_1$, $R_2$ and $R_3$ is unsubstituted. In another aspect this ring is substituted by one or two substituents selected from hydroxy, oxo, carbonyl, (1-4C)alkoxycarbonyl or one of the following:

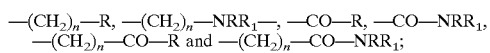

wherein n is 1 or 2;

R and $R_1$ are independently selected from hydrogen, (1-4C)alkyl, (2-4C)alkenyl, (2-4C)alkynyl, hydroxy(1-4C)alkyl, carboxy(1-4C)alkyl and (1-4C) alkoxycarbonyl-(1-4C)alkyl or where possible R and $R_1$ may together form a 5- or 6-membered optionally substituted heterocyclic ring which may include in addition to the nitrogen atom to which R and $R_1$ are attached 1 or 2 additional heteroatoms selected from nitrogen, oxygen and sulphur.

In a particular aspect the heterocyclic rings formed by R and $R_1$ are preferably selected from pyrrolidin-1-yl, imidazolin-1-yl, piperidin-1 yl, piperazin-1-yl, 4-morpholino and 4-thiomorpholino. In a particular aspect the heterocyclic ring formed by R and $R_1$ may be unsubstituted. In an alternative aspect the ring formed by R and $R_1$ is substituted by 1 or 2 substituents selected from oxo, hydroxy, carboxy and (1-4C)alkyl, preferably oxo, hydroxy, and carboxy.

In a particular aspect $X_2$ is $SO_2$, $CH_2$ or CO. Preferably $X_2$ is $SO_2$.

In one aspect Q is unsubstituted. In another aspect Q is substituted by one, two or three substituents selected from halo, trifluoromethyl, trifluoromethoxy, cyano, hydroxy, amino, nitro, trifluoromethanesulphonyl, carboxy, carbamoyl, (1-4C)alkyl, (2-4C)alkenyl, (2-4C)alkynyl, (1-4C)alkoxy, (2-4C)alkenyloxy, (2-4C)alkynyloxy, (1-4C) alkylthio, (1-4C)alkylsulphinyl, (1-4C)alkylsulphonyl, (1-4C)alkylamino, di-(1-4C)alkylamino, (1-4C) alkoxycarbonyl, N-(1-4C)alkylcarbamoyl, N,N-di-(1-4C) alkylcarbamoyl, (2-4C)alkanoyl, (2-4C)alkanoylamino, hydroxy-(1-4C)alkyl, (1-4C)alkoxy-(1-4C)alkyl, carboxy-(1-4C)alkyl, (1-4C)alkoxycarbonyl-(1-4C)alkyl, carbamoyl-(1-4C)alkyl, N-(1-4C)alkylcarbamoyl-(1-4C)alkyl, N,N-di-(1-4C)alkylcarbamoyl-(1-4C)alkyl, phenyl, heteroaryl, phenoxy, phenylthio, phenylsulphinyl, phenylsulphonyl, benzyl, benzoyl, heteroaryloxy, heteroarylthio, heteroarylsulphinyl and heteroarylsulphonyl, and wherein said heteroaryl substituent or the heteroaryl group is a heteroaryl-containing substituent comprises a 5- or 6-membered monocyclic heteroaryl ring containing up to 3 heteroatoms selected from nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1, 2 or 3 substituents selected from halogeno, trifluoromethyl, cyano, hydroxy, amino, nitro, carboxy, carbamoyl, (1-4C)alkyl, (1-4C)alkoxy, (1-4C)alkylamino, di-(1-4C)alkylamino, (1-4C)alkoxycarbonyl, N-(1-4C)alkylcarbamoyl, N,N-di-(1-4C)alkylcarbamoyl and (2-4C)alkanoylamino.

A suitable value for Q when it is naphthyl is, for example, 1-naphthyl or 2-naphthyl; when it is phenyl-(1-4C)alkyl is, for example, benzyl, phenylethyl and 3-phenylpropyl, when it is phenyl-(2-4C)alkenyl is, for example, styryl, cinnamyl or 3-phenylprop-2-enyl; and when it is phenyl-(2-4C) alkynyl is, for example, 2-phenylethynyl, 3-phenylprop-2-ynyl and 3-phenylprop-1-ynyl.

A suitable value for Q when it is a heterocyclic moiety containing up to 4 heteroatoms selected from nitrogen, oxygen and sulphur is, for example, a 5- or 6-membered heterocyclic moiety which is a single ring or is fused to one or two benzo rings such as furyl, benzofuranyl, tetrahydrofuryl, chromanyl, thienyl, benzothienyl, pyridyl, piperidinyl, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, quinoxalinyl, quinazolinyl, cinnolinyl, pyrrolyl, pyrrolidinyl, indolyl, indolinyl, imidazolyl, benzimidazolyl, pyrazolyl, indazolyl, oxazolyl, benzoxazolyl, isoxazolyl, thiazolyl, benzothiazolyl, isothiazolyl, morpholinyl, 4H-1,4-benzoxazinyl, 4H-1,4-benzothiazinyl, 1,2,3-triazolyl, oxadiazolyl, furazanyl, thiadiasolyl, tetrazolyl, dibenzofuranyl and dibenzothienyl, which may be attached through any available position including, for an appropriate $X_2$ group such as, for example, $SO_2$, $C(R^5)_2$ or CO, through any available nitrogen atom. Q may optionally bear up to three substituents including a substituent or any available nitrogen atom.

A suitable value for the heteroaryl substituent on Q or the heteroaryl group in a heteroaryl-containing substituent on Q which comprises a 5- or 6-membered monocyclic heteroaryl ring containing up to 3 heteroatoms selected from oxygen, nitrogen and sulphur is, for example, furyl, thienyl, pyridyl, pyrazinyl, pyrimidinyl, pyridazinyl, pyrrolyl, imidazolyl, pyrazolyl, oxazolyl, isoxazolyl, thiazolyl, isothiazolyl, 1,2,3-triazolyl, 1,2,4-triazolyl, oxadiazolyl, furazanyl and thiadiazolyl which may be attached through any available position including through any available nitrogen atom.

Suitable values for optional substituents for the ring formed on Q are:

for (1-4C)alkyl: methyl, ethyl and propyl;

for (1-4C)alkoxycarbonyl: methoxycarbonyl, ethoxycarbonyl, propoxycarbonyl and tert-butoxycarbonyl;

for N-(1-4C)alkylcarbamoyl: N-methylcarbamoyl, N-ethylcarbamoyl and N-propylcarbamoyl;

for N,N-di-[(1-4C)alkyl]carbamoyl: N,N-dimethylcarbamoyl, N-ethyl-N-methylcarbamoyl and N,N-diethylcarbamoyl;

for 4-(1-4C)alkylpiperazin-1-ylcarbonyl: 4-methylpiperazin-1-ylcarbonyl and 4-ethylpiperazin-1-ylcarbonyl;

for hydroxy-(1-4C)alkyl: hydroxymethyl, 1-hydroxyethyl, 2-hydroxyethyl and 3-hydroxypropyl;

for (1-4C)alkoxy-(1-4C)alkyl: methoxymethyl, ethoxymethyl, 1-methoxymethyl, 2-methoxyethyl, 2-ethoxyethyl and 3-methoxypropyl;

for carboxy-(1-4C)alkyl: carboxymethyl, 1-carboxyethyl, 2-carboxyethyl and 3-carboxypropyl;

for (1-4C)alkoxycarbonyl-(1-4C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbamoyl-(1-4C)alkyl: carbamoylmethyl, 1-carbamoylethyl, 2-carbamoylethyl and 3-carbamoylpropyl;

for N-(1-4C)alkylcarbamoyl-(1-4C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[(1-4C)alkyl]carbamoyl-(1-4C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl;

for pyrrolidin-1-ylcarbonyl-(1-4C)alkyl: pyrrolidin-1-carbonylmethyl, 1-(pyrrolidin-1-ylcarbonyl)ethyl and 2-(pyrrolidin-1-ylcarbonyl)ethyl;

for piperidinocarbonyl-(1-4C)alkyl: piperidinocarbonylmethyl, 1-(piperidinocarbonyl)ethyl and 2-(piperidinocarbonyl)ethyl;

for morpholinocarbonyl-(1-4C)alkyl: morpholinocarbonylmethyl, 1-(morpholinocarbonyl)ethyl and 2-(morpholinocarbonyl)ethyl;

for piperazin-1-ylcarbonyl-(1-4C)alkyl: piperazin-1-ylcarbonylmethyl, 1-(piperazin-1-ylcarbonyl)ethyl and 2-(piperazin-1-ylcarbonyl)ethyl;

for 4-(1-4C)alkylpiperazin-1-ylcarbonyl-(1-4C)alkyl: 4-methylpiperazin-1-ylcarbonylmethyl, 4-ethylpiperazin-1-ylcarbonylmethyl, 2-(4-methylpiperazin-1-ylcarbonyl)ethyl and 2-(4-ethylpiperazin-1-ylcarbonyl)ethyl.

For suitable value for a (1-4C)alkyl group which may be present on a heterocyclic group in a substituent on $L_1$ or the ring formed when $R_2$ and $R_3$ are linked is, for example, methyl, ethyl or propyl.

Suitable values for substituents (where applicable) which may be present on a eterocyclic or phenyl group within a substituent on Ar, on Q or on a phenyl- or heteroaryl-containing substituent on Q include, for example:

for halo: fluoro, chloro, bromo;

for (1-4C)alkyl: methyl, ethyl, propyl, butyl;

for (1-4C)alkoxy: methoxy, ethoxy;

for (1-4C)alkylamino: methylamino, ethylamino;

for di-(1-4C)alkylamino: dimethylamino, diethylamino;

for (2-4C)alkenyl: vinyl and allyl;

for (2-4C)alkynyl: ethynyl and prop-2-ynyl;

for (2-4C)alkenyloxy: vinyloxy and allyloxy;

for (2-4C)alkynyloxy: ethynyloxy and prop-2-ynyloxy;

for 4-(1-4C)alkylpiperazin-1-yl: 4-methylpiperazin-1-yl and 4-ethylpiperazin-1-yl;

for (1-4C)alkylthio: methylthio, ethylthio and propylthio;

for (1-4C)alkylsulphinyl: methylsulphinyl, ethylsulphinyl and propylsulphinyl;

for (1-4C)alkylsulphonyl: methylsulphonyl, ethylsulphonyl and propylsulphonyl;

for (2-4C)alkanoylamino: acetamido, propionamido and butyramido;

for (1-4C)alkanesulphonaido: methanesulphonamido and ethanesulphonamido;

for (1-4C)alkoxycarbonyl: methoxycarbonyl, ethoxycarbonyl, propoxycarbonyl and tert-butoxycarbonyl;

for N-(1-4C)alkylcarbamoyl: N-methylcarbamoyl, N-ethylcarbamoyl and N-propylcarbamoyl;

for N,N-di-[(1-4C)alkyl]carbamoyl: N,N-dimethylcarbamoyl, N-ethyl-N-methylcarbamoyl and N,N-diethylcarbamoyl;

for 4-(1-4C)alkylpiperazin-1-ylcarbonyl: 4-methylpiperazin-1-ylcarbonyl and 4-ethylpiperazin-1-ylcarbonyl;

for (1-4C)alkanesulphonamidocarbonyl: methanesulphonamidocarbonyl and ethanesulphonamidocarbonyl;

for (2-4C)alkanoyl: acetyl, propionyl and butyryl;

for hydroxy-(1-4C)alkyl: hydroxymethyl, 1-hydroxyethyl, 2-hydroxyethyl and 3-hydroxypropyl;

for (1-4C)alkoxy-(1-4C)alkyl: methoxymethyl, ethoxymethyl, 1-methoxymethyl, 2-methoxyethyl, 2-ethoxyethyl and 3-methoxypropyl;

for carboxy-(1-4C)alkyl: carboxymethyl, 1-carboxyethyl, 2-carboxyethyl and 3-carboxypropyl;

for (1-4C)alkoxycarbonyl-(1-4C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbamoyl-(1-4C)alkyl: carbamoylmethyl, 1-carbamoylethyl, 2-carbamoylethyl and 3-carbamoylpropyl;

for N-(1-4C)alkylcarbamoyl-(1-4C)alkyl: N-methylcarbamoylmethyl, N-ethylcarbamoylmethyl, N-propylcarbamoylmethyl, 1-(N-methylcarbamoyl) ethyl, 1-N-ethylcarbamoyl)ethyl, 2-N-methylcarbamoyl)ethyl, 2-(N-ethylcarbamoyl)ethyl and 3-(N-methylcarbamoyl)propyl;

for N,N-di-[(1-4C)alkyl]carbamoyl-(1-4C)alkyl: N,N-dimethylcarbamoylmethyl, N-ethyl-N-methylcarbamoylmethyl, N,N-diethylcarbamoylmethyl, 1-(N,N-dimethylcarbamoyl) ethyl, 1-(N,N-diethylcarbamoyl)ethyl, 2-(N,N-dimethylcarbamoyl)ethyl, 2-(N,N-diethylcarbamoyl) ethyl and 3-(N,N-dimethylcarbamoyl)propyl;

A preferred class of compounds of the present invention is that wherein:

A is pyridyl, pyrimidinyl or pyridazinyl;

B is pyridinediyl, pyrimidinediyl or pyridazinediyl;

$X_1$ is CO, $SO_2$ or $CH_2$, ideally CO;

$T_1$ and $T_2$ are both N;

$L_1$ is ethylene or propylene;

$R_2$ and $R_3$ are joined to form an ethylene or propylene or methylenecarbonyl group;

wherein the heterocyclic ring formed by $T_1$, $T_2$, $L_1$, $R_2$ and $R_3$ is unsubstituted or is substituted;

$X_2$ is $SO_2$;

Q is styryl optionally substituted (preferably 4-substituted), naphthyl optionally substituted (preferably 6-substituted) or is phenyl optionally substituted (preferably 4-substituted) by fluoro, chloro or bromo;

and pharmaceutically-acceptable salts thereof.

A particular compound of the invention is:

1-(6-bromonaphth-2-ylsulphonyl)-4-[6-(4-pyridyl)-nicotinoyl]piperazine;

1-(6-bromonaphth-2-ylsulphonyl)-4-[6-(4-pyridyl)-pyridazin-3-ylcarbonyl]piperazine;

1-(6-bromonaphth-2-ylsulphonyl)-4-[5-(4-pyridyl)-2-pyridylcarbonyl]piperazine; or 1-(6-chloronaphth-2-ylsulphonyl)-4-[5-(4-pyridyl)-2-pyridylcarbonyl]piperazine.

Compounds of formula I, or pharmaceutically-acceptable salt thereof, may be prepared by any process known to be applicable to the preparation of related compounds. Such procedures are provided as a further feature of the invention and are illustrated by the following representative processes in which, unless otherwise stated A, $B_1$, $B_2$, $B_3$, $B_4$, $X_1$, $T_1$, $T_2$, $L_1$, $R_2$, $R_3$, $X_2$ and Q have any of the meanings defined hereinbefore wherein any functional group, for example amino, alkylamino, carboxy or hydroxy, is optionally protected by a protecting group which may be removed when necessary.

Necessary starting materials may be obtained by standard procedures of organic chemistry.

According to another aspect, the present invention provides a process for preparing a compound of formula I or a pharmaceutically acceptable salt thereof, which comprises:

(a) For the production of compounds of the formula (1) wherein $T_1$ is N and $X_1$ is CO, the reaction, conveniently in the presence of a suitable base, of an amine of formula (II)

$$NH(R_2)—L_1—T_2(R_3)—X_2—Q \qquad (II)$$

with an acid of the formula III

(III)

or a reactive derivative thereof.

A suitable reactive derivative of an acid of formula (III) is, for example, an acyl halide, for example an acyl chloride formed by the reaction of the acid and an inorganic acid chloride, for example thionyl chloride; a mixed anhydride, for example an anhydride formed by the reaction of the acid with a chloroformate such as isobutyl chloroformate or with an activated amide such as 1,1'-carbonyldiimidazole; an active ester, for example an ester formed by the reaction of the acid and a phenol such as pentafluorophenol, an ester such as pentafluorophenyl trifluoroacetate or an alcohol such as N-hydroxybenzotriazole or N-hydroxysuccinimide; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethyl-carbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl, or an arylmethyl, for example benzyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). An arylmethyl, such as benzyl may be removed by hydrogenation over a catalyst such as palladium-on-carbon. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

(b) For the production of those compounds of formula I wherein $T_1$ is CH and $X_1$ is O by the reaction, conveniently in the presence of a suitable coupling agent, of a compound of the formula (IV):

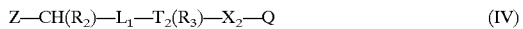

$$Z\text{—}CH(R_2)\text{—}L_1\text{—}T_2(R_3)\text{—}X_2\text{—}Q \qquad (IV)$$

wherein Z is a displaceable group, with a compound of formula (V):

(V)

A suitable value for the displaceable group Z is, for example, a halogeno or sulphonyloxy group, for example a fluoro, chloro, bromo, mesyloxy or 4-tolylsulphonyloxy group.

A suitable reagent for the coupling reaction when Z is a halogeno or sulphonyloxy group is, for example, a suitable base, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, $-10°$ to $150°$ C., conveniently at or near ambient temperature.

An analogous procedure may be employed for the preparation of those compounds of the formula (I) wherein $T_1$ is CH and $X_1$ is a group of the formula S.

A suitable reagent for the coupling reaction of the alcohol of the formula (V) wherein Z is a hydroxy group, where the hydroxy group is converted in situ to a displaceable group as defined above, is, for example, the reagent obtained when said alcohol is reacted with a di-(1–4C)alkyl azodicarboxylate in the presence of a triarylphosphine or tri-(1–4C)alkylphosphine, for example with diethyl azodicarboxylate in the presence of triphenylphosphine or tributylphosphine. The reaction is preferably performed in a suitable inert solvent or diluent, for example acetone, 1,2-dimethoxyethane or tetrahydrofuran, and at a temperature in the range, for example, $10°$ to $80°$ C., conveniently at or near ambient temperature.

(c) For the production of those compounds of formula (I) wherein $T_1$ is N and $X_1$ is $CH(R_4)$, the reductive amination of a keto compound of formula (VI):

(VI)

with an amine of the formula (II) as defined above.

Any reducing agent known in the art for promoting a reductive amination reaction may be employed. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride. The reaction is performed at a temperature in the range, for example, $10°$ to $80°$ C., conveniently at or near ambient temperature.

(d) The reaction of a compound of formula (VII):

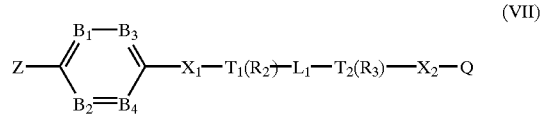

(VII)

wherein Z is a displaceable group such as halo, with an activated derivative of heterocyclic ring A. Suitable activated derivatives include metalised derivatives, such as with zinc or tin, and borane derivatives. The activated derivative of heterocyclic ring A is reacted with a compound of formula (VII) to effect cross coupling where Z is a halo group, such as iodo, bromo or chloro and triflate. Suitably the reaction is catalysed by use of a transition state metal catalyst, such as palladium, e.g. tetrakis (triphenylphosphine) palladium (0).

Alternatively it is possible that ring A contains the displaceable group Z and the ring containing $B_1$ to $B_4$ is activated, as described above.

Compounds of formula (VII) not suitable for for this method are those which contain halo substituents on A, B, or $L_1$.

(e) By forming A ring on compounds of formula (VII), wherein Z is a functional group capable of cyclisation. Suitable reagents and conditions are described below in the preparation of compounds of formula (X) by cyclisation.

(f) For the production of compounds wherein $T_2$ is N, the reaction of a compound of the formula (VIII):

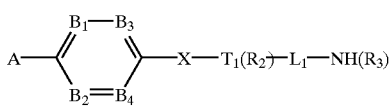
(VIII)

with a compound of the formula (IX):

(IX)

wherein Z is a displaceable group for example chloro, under conditions similar to those of process variant (a) above.

(g) For the production of compounds wherein $T_1$ is N and $X_1$ is SO or $SO_2$, the reaction of a compound of the formula (II) as defined above:
with a compound of the formula (X):

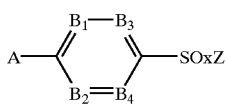
(X)

wherein X is one or two and Z is a displaceable group; under appropriate conventional coupling conditions, similar to those of process variant (a) above.

(h) For producing compounds of formula I by coupling $T_2$ to Q and thus preparing the $-T_2-X_2-Q$ moiety, methods analogous to those described in process variants (a), (c) and (f) for preparing the $B-X_1-T_1$-moiety may be employed.

(i) For the production of compounds of the formula (I) wherein $X_1$ is a group of the formula SO, $SO_2$, wherein the ring containing $B_1$ to $B_4$ bears a 1-oxothiomorpholino or 1,1-dioxothiomorpholino group or a substituent which contains a (1–4C)alkylsulphinyl, (1–4C)alkylsulphonyl, 1-oxothiomorpholino or 1,1-dioxothiomorpholino group, wherein $X_2$ is a group of the formula SO or $SO_2$ wherein Q bears a (1–4C)alkylsulphinyl, (1–4C)alkylsulphonyl, phenylsulphinyl, phenylsulphonyl, heteroarylsulphinyl or heteroarylsulphonyl group, the oxidation of the corresponding compound of the formula I wherein $X_1$, $X_2$, or both $X_1$ and $X_2$ is S.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15 to 35° C. Suitable reagents and conditions are described in, for example. Page G. O.: Synth. Commun. 23, (1993) 6, 765–769. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound. Those compounds of formula I which contain oxygen labile groups (such as A ring is pyridyl) are probably not suitable intermediates for this process step, unless oxidation of such groups is desired.

Compounds of formula (II) where $T_2$ is N may be prepared by the reaction of a compound of the formula (XI)

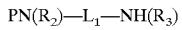
(XI)

wherein P is a protecting group, with a compound of formula (IX), as defined above, in an analogous manner as described above in method (e) above, and subsequently removing the protecting group. In addition compounds of formula (II) may be prepared in an analogous manner as described above in methods (g) and (h).

Compounds of formula (IV) may be prepared in an analogous manner as described for the preparation of compounds of formula (II).

Compounds of formula (III) may be prepared by the coupling of a compound of formula (XII), wherein Z is a displaceable group, preferably halo,

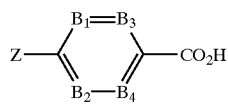
(XII)

with an activated derivative of the heterocyclic ring A via a coupling reaction as described in method (d) above. Ideally the reaction is catalysed, such as with a palladium catalyst. Suitable reagents and conditions are described in a review article Harvey R. G. Organic Preparations and Procedures International, Vol. 29, (1997), 139.

Activated derivatives of heterocyclic ring A include metalised derivatives, such as with zinc or tin, borane derivatives and stannyl derivatives. Formation of the activated form desired is typically by substitution reactions. The activating group is added to the ring in place of a suitable leaving group or atom, such as halo or triflate. Suitable reagents and conditions are described in Shikara M. et. al.; Chem. Pharm. Bull.; 33(11), 4755–4763 (1985); Sandosham J. et. al.; Heterocycles, Vol. 37, No. 1, p501, (1994); and Salamoto T. et. al.; Tetrahedron; Vol. 49, No. 43, 9713–9720, (1993).

Alternatively compounds of formula (III) may be prepared by forming A rings on compounds of formula (XII) by cyclisation reaction, wherein Z is a functional group capable of cyclisation. Suitable reagents and conditions are described in Bredereck H. Chem. Ber.; 96, 1505, (1963); Fuchigami, T., Bull. Chem. Soc. Jpn., 49, p3607, (1976); Huffman, K. R., J. Org. Chem., 28, p1812, (1963); Palusso, G., Gazz. Chim. Ital., 90, p1290, (1960) and Ainsworth C. J., Heterocycl. Chem., 3, p470, (1966). Processes suitable for synthesis of starting materials in such cyclisation reactions are described in Zhang M. Q. et al; J. Heterocyclic. Chem.; 28, 673, (1991) and Kosugi, M. et al., Bull. Chem. Soc. Jpn., 60, 767–768 (1987).

Compounds of formula (XII) may be prepared via ring formation, such as described in Church R, et al.; J. Org. Chem., 60, 3750–3758, (1995) and Falck-Penderson M. L., et. al.; Acta Chem. Scand., 47, 63–67, (1993). Compounds formed by such reactions are also suitable starting materials for preparation of activated derivatives of the heterocyclic ring A, as described above.

Compounds of formula (V), (VI) and (X) may be prepared in an analogous manner as described for preparing compounds of formula (III), and if required with the use of suitable protecting groups.

Compounds of formula (VII) wherein $T_2$ is N may be prepared by the reaction of a compound of the formula (XIII)

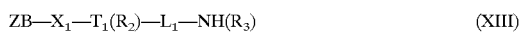

$$ZB-X_1-T_1(R_2)-L_1-NH(R_3) \quad \text{(XIII)}$$

with a compound of formula (IX), as defined above, in an analogous manner as described above in method (f).

Compounds of formula (XIII) wherein $T_1$ is N and $X_1$ is CO may be prepared by the reaction of a compound of the formula (XIV)

$$HN(R_2)-L_1-T_2(R_3)P \quad \text{(XIV)}$$

wherein when $T_2$ is CH then P is H or when $T_2$ is N then P is a protecting group, with a compound of the formula (XV)

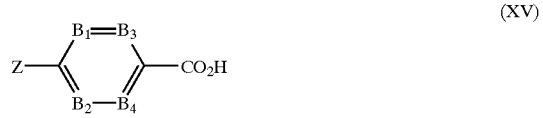

in an analogous manner is described in method (a) above and subsequently, where P is a protecting group, effecting removal of the protecting group.

Compounds of formula (XIII) wherein $T_1$ is CH and $X_1$ is O may be prepared by the reaction of a compound of formula (XVI)

$$Z-CH(R_2)-L_1-T_2(R_3) \quad \text{(XVI)}$$

wherein Z is a displaceable group with phenol in an analogous method as described in method (b) above Compounds of formula (X), where x is 1 or 2, may be prepared by oxidation of compound of formula (X), where $X_2$ is S, in an analogous method as described in method (h) above. Suitable reagents and conditions are described in Newman, M. S., et. al., Organic Synthesis, Vol. 51, p139. Methods for preparation of the thio analogues of Q are described in Kharasch, N. et. al., J. Am. Chem. Soc., 73, p3240, (1951).

When a pharmaceutically-acceptable salt of a compound of the formula I is required, it may be obtained, for example, by reaction of said compound with a suitable acid or base using a conventional procedure.

When an optically active form of a compound of the formula I is required, it may be obtained, for example, by carrying out one of the aforesaid procedures using an optically active starting material or by resolution of a racemic form of said compound using a conventional procedure, for example by the formation of diastereomeric salts, use of chromatographic techniques, conversion using chirally specific enzymatic processes, or by addition of temporary extra chiral group to aid separation.

As stated previously, the compounds of the formula I are inhibitors of the enzyme Factor Xa. The effects of this inhibition may be demonstrated using one or more of the standard procedures set out hereinafter.

a) Measurement of Factor Xa Inhibition

An in vitro assay system is carried out based on the method of Kettner et al., J. Biol. Chem., 1990, 265, 18289–18297, whereby various concentrations of a test compound are dissolved in a pH 7.5 buffer containing 0.5% of a polyethylene glycol (PEG 6000) and incubated at 37° C. with human Factor Xa (0.001 Units/ml, 0.3 ml) for 15 minutes. The chromogenic substrate S-2765 (Kabi Vitrum AB, 20 $\mu$M) is added and the mixture is incubated at 37° C. for 20 minutes whilst the absorbance at 405 nm is measured. The maximum reaction velocity (Vmax) is determined and compared with that of a control sample containing no test compound. Inhibitor potency is expressed as an $IC_{50}$ value.

b) Measurement of Thrombin Inhibition

The procedure of method a) is repeated except that human thrombin (0.005 Units/ml) and the chromogenic substrate S-2238 (Kabi Vitrum AB, 7 $\mu$M) are employed.

c) Measurement of Anticoagulant Activity

An in vitro assay whereby human, rat or rabbit venous blood is collected and added directly to a sodium citrate solution (3.2 g/100 ml, 9 parts blood to 1 part citrate solution). Blood plasma is prepared by centrifugation (1000 g, 15 minutes) and stored at 2–4° C. Conventional prothrombin time (PT) tests are carried out in the presence of various concentrations of a test compound and the concentration of test compound required to double the clotting time, hereinafter referred to as CT2, is determined. In the PT test, the test compound and blood plasma are incubated at 37° C. for 10 minutes. Tissue thromboplastin with calcium (Sigma Limited. Poole, England) is added and fibrin formation and the time required for a clot to form are determined.

d) An ex vivo Assay of Anticoagulant Activity

The test compound is administered intravenously or orally to a group of Alderley Park Wistar rats. At various times thereafter animals are anaesthetised, blood is collected and PT coagulation assays analogous to those described hereinbefore are conducted.

e) An in vivo Measurement of Antithrombotic Activity

Thrombus formation is induced using an analogous method to that described by Vogel et al., Thromb. Research, 1989, 54, 399–410. A group of Alderley Park Wistar rats is anaesthetised and surgery is performed to expose the vena cava. Collateral veins are ligated and two loose sutures are located, 0.7 cm apart, round the interior vena cava. Test compound is administered intravenously or orally. At an appropriate time thereafter tissue thromboplastin (30 $\mu$l/kg) is administered via the jugular vein and, after 10 seconds, the two sutures are tightened to induce stasis within the ligated portion of vena cava. After 10 minutes the ligated tissue is excised and the thrombus therein is isolated, blotted and weighed.

(f) Rat Disseminated Intravascular Coagulation in vivo activity test

Fasted male Alderley Park rats (300–450 g) are pre-dosed by oral gavage (5 mls/kg) with compound or vehicle (5% DMSO/PEG200) at various times before being anaesthetised with Intraval® (120 mg/kg i.p.). The left jugular vein and the right carotid artery are exposed and cannulated. A 1 mL blood sample is taken from the carotid cannula into 3.2% trisodium citrate. 0.5 mL of the whole blood is then treated with EDTA and used for platelet count determination whilst the remainder is centrifuged (5 mins, 20000 g) and the resultant plasma frozen for subsequent drug level, fibrinogen or thrombin antithrombin (TAT) complex determinations. Recombinant human tissue factor (Dade Innovin Cat.B4212-50), reconstituted to the manufacturers specification, is infused (2 mL/kg/hr) into the venous cannula for 60 minutes. Immediately after the infusion is stopped a 2 mL blood sample is taken and platelet count, drug level, plasma fibrinogen concentration and TAT complex are determined as before. Platelet counting is performed using a Coulter T540 blood analyser. Plasma fibrinogen and TAT levels are determining using a clotting assay (Sigma Cat.880-B) and TAT ELISA (Behring) respectively. The plasma concentration of the compound is bioassayed using human Factor Xa and a chromogenic substrate S2765 (Kabi), extrapolated from a standard curve (Fragmin) and expressed in Anti-Factor Xa units. The data is analysed as follows; tissue factor-induced reductions in platelet count are normalised with respect to pre-dose platelet count and drug activity expressed as a percent inhibition of tissue factor-induced thrombocytopenia when compared to vehicle treated animals. Compounds are active if there is statistically significant ($p>0.05$) inhibition of TF-induced thrombocytopenia.

In general compounds of the formula I possess activity at the following concentrations or doses in at least one of the above tests a) to c):

test a): $IC_{50}$ (Factor Xa) in the range, for example, 0.001–25 $\mu$M;

test b): $IC_{50}$ (thrombin), for example, greater than 40 $\mu$M;

test c): CT2 (PT) in the range, for example, 0.1–50 $\mu$M.

According to a further feature of the invention there is provided a pharmaceutical composition which comprises a heterocyclic derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a heterocyclic derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocyclic derivative of the formula I, or a pharmaceutically-acceptable salt thereof, for use in a method of treatment of the human or animal body by therapy.

The invention also includes the use of such an active ingredient in the production of a medicament for use in:

(i) producing a Factor Xa inhibitory effect;

(ii) producing an anticoagulant effect;

(iii) producing an antithrombotic effect;

(iv) treating a Factor Xa mediated disease or medical condition;

(v) treating a thrombosis mediated disease or medical condition;

(vi) treating coagulation disorders; and/or (vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of the formula I will naturally vary according to the nature and severity of the medical condition, the age and sex of the animal or patient being treated and the route of administration, according to well known principles of medicine. As mentioned above, compounds of the formula I are useful in the treatment or prevention of a variety of medical disorders where anticoagulant therapy is indicated. In using a compound of the formula I for such a purpose, it will generally be administered so that a daily dose in the range, for example, 0.5 to 500 mg/kg body weight is received, given if required in divided doses. In general lower doses will be administered when a parenteral route is employed, for example a dose for intravenous administration in the range, for example, 0.5 to 50 mg/kg body weight will generally be used. For preferred and especially preferred compounds of the invention, in general, lower doses will be employed, for example a daily dose in the range, for example, 0.5 to 10 mg/kg body weight.

Although the compounds of the formula I are primarily of value as therapeutic or prophylactic agents for use in warm-blooded animals including man, they are also useful whenever it is required to produce an anticoagulant effect, for example during the ex-vivo storage of whole blood or in the development of biological tests for compounds having anticoagulant properties.

The compounds of the invention may be administered as a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known antihypertensive agent.

The invention will now be illustrated in the following Examples in which, unless otherwise stated:

(i) evaporations were carried out by rotary evaporation in vacuo and work-up procedures were carried out after removal of residual solids by filtration;

(ii) operations were carried out at room temperature, that is in the range 18–25° C. and under an atmosphere of an inert gat such as argon;

(iii) column chromatography (by the flash procedure) and medium pressure liquid chromatography (MPLC) were generally performed on Merck Kieselgel silica (Art.

9385) or Merck Lichroprep RP-18 (Art. 9303) reversed-phase silica obtained from E. Merck, Darmstadt, Germany; alternatively high pressure liquid chromatography (HPLC) was performed on a Dynamax C-18 60 Å preparative reversed-phase column;

(iv) yields are given for illustration only and are not necessarily the maximum attainable;

(v) the end-products of the formula I have satisfactory microanalyses and their structures were confirmed by nuclear magnetic resonance (NMR) and mass spectral techniques; unless otherwise stated, $CD_3SOCD_3$ solutions of the end-products of the formula I were used for the determination of NMR spectral data, chemical shift values were measured on the delta scale; the following abbreviations have been used; s, singlet; d, doublet; t, triplet; q, quartet; m, multiplet;

(vi) intermediates were not generally fully characterised and purity was assessed by thin layer chromatographic, infra-red (IR) or NMR analysis;

(vii) melting points were determined using a Mettler SP62 automatic melting point apparatus or an oil-bath apparatus; melting points for the end-products of the formula I were generally determined after crystallisation form a conventional organic solvent such as ethanol, methanol, acetone, ether or hexane, alone or in admixture; and (viii) the following abbreviations have been used:

| (viii) the following abbreviations have been used:- | |
| --- | --- |
| DMF | N,N-dimethylformamide; |
| EToAc | ethyl acetate; |
| DMSO | dimethylsulphoxide. |

EXAMPLE 1

1) 1-(6-bromonaphth-2-ylsulphonyl)-4-[6-(4-pyridyl)-nicotinoyl]piperazine

To a solution of 450 mg (1.38 mmol) 6-(4-pyridyl)-nicotinic-[4-(1-tert-butyloxycarbonyl)-piperazine]amide in 10 ml dry $CH_2Cl_2$ was added at room temperature 10 ml trifluoroacetic acid. The resulting mixture was stirred at room temperature until no further gas evolution was observed. At this point all volatile components were removed under vacuum and the resultant oily gum was dried on the high vacuum pump for 1 hour. The intermediate was then re-dissolved in dry dichloromethane (15 ml). Triethylamine was added until the gas phase above the solution showed an alkaline reaction with wet indicator paper. A further equivalent of triethylamine was added and then 425 mg (1.38 mmol) of 6-bromonaphth-2-ylsulphonylchloride was added as a solution in dry dichloromethane (2 ml). The resulting homogeneous mixture was stirred at room temperature over night before the reaction was quenched by the addition of 10 ml saturated aqueous ammonium chloride. The organic phase was separated and the aqueous phase was extracted three times with dichloromethane (5 ml). The combined organic extracts were dried over $MgSO_4$, concentrated in vacuo and purified by flash column chromatography on silica (5% $MeOH$/95% $CH_2Cl_2$). The purified compound could be recrystallized from ethyl acetate to yield 440 mg of 1-(6-bromonaphth-2-ylsulphonyl)-4-[6-(4-pyridyl)-nicotinoyl]piperazine as a fine pale yellow crystalline solid.

$^1$H NMR (300 MHz, $CDCl_3$) $\delta$=3.00–3.40 (broad, 4H), $\delta$=3.48–4.00 (broad, 4H), $\delta$=7.70–7.78 (m, 2H), $\delta$=7.80–7.86 (m, 6H), $\delta$=7.87–7.96 (m, 1H), $\delta$=8.16–8.17 (m, 1H), $\delta$=8.29–8.32 (m, 1H), $\delta$=8.62–8.66 (m, 1H), $\delta$=8.72–8.80 (m, 2H). Solvent peaks Ethyl Acetate 1.25 (t), 2.04 (s), 4.12 (q) ~6 mol %; Dichloromethane 5.3 (s) ~3 mol %. Water 1.60 (s) unknown amount. MS (ES+) 537/539 $(M+H)^+$, 267, 190, 183, 106, 78. Elemental Analysis: $C_{25}H_{21}BrN_4O_3S$ required C=55.9, H=3.9, N=10.4, Br=14.9, S=6.0. found C=55.3, H=4.0, N=10.1, Br=14.2, S=5.9, $H_2O$=0.1. mp 193.5° C. (method DSC)

2) 6-(4-Pyridyl)-nicotinic-[4-(1-tert-butyloxycarbonyl)-piperazine]amide

To a suspension of 834 mg (5.67 mmol) diethyl-pyridylborane in 20 ml of degassed, dry tetrahydrofuran was added to room temperature under inert gas atmosphere 637 mg (11.3 mmol) potassium hydroxide, 1.01 g (2.73 mmol) $Bu_4NI$ and 1.85 g (5.67 mmol) 6-chloro-nicotinic-[4-(1-tert-butyloxycarbonyl)-piperazine]amide sequentially before 656 mg (0.56 mmol) of tetrakis (triphenylphosphine) palladium (0) was added. The resulting suspension was heated to 60° C. for 2–3 hours. The resulting dark brown suspension was cooled to room temperature before the catalyst was removed by filtration through celite. The filtrate was then diluted with ethyl acetate and washed with 10 ml of saturated aqueous sodium chloride solution. The organic phase was separated and the aqueous phase was extracted three times with ethyl acetate. The combined organic extracts were treated with charcoal, dried over $MgSO_4$, concentrated in vacuo and purified by flash column chromatography from silica gel (6% $MeOH$/94% $CH_2Cl_2$). After purification, 1.68 g of the product were obtained as a light brown foam which contained minor impurities and an occasion crystallised very slowly on standing to give a pale brown solid.

$^1$H NMR ($CDCl_3$) $\delta$=1.44 (s, 9H), $\delta$=3.38–3.82 (broad, 8H), $\delta$=7.88 (m, 4H), $\delta$=8.75 (m, 3H), MS (ES+)=369.4 $(M+H)^-$.

3) 6-Chloro-nicotinic-[4-(1-tert-butyloxycarbonyl)-piperazine]amide

To a suspension of 18.7 g (118 mmol) of 6-chloro nicotinic acid and 22.1 g (118 mmol) and (1-tert-butyloxycarbonyl)-piperazine in 500 ml of dry dichloromethane was added 25 g (130 mmol) 1-(3-dimethylaminopropyl)-3-ethylcarbodiimide hydrochloride and 36 ml (236 mmol) dry triethylamine at room temperature. The resulting pale brown solution was stirred at room temperature for 16 hours before being quenched by the addition of 50 ml saturated aqueous ammonium chloride solution. The organic phase was separated and the aqueous phase was extracted three times with dichloromethane. The combined organic extracts were dried over anhydrous $MgSO_4$, concentrated in vacuo and purified in flash column chromatography from silica gel to yield 30.5 g of colourless crystals of the desired 6-chloro-nicotinic-[4-(1-tert-butyloxycarbonyl)-piperazine]amide and some 3.5 g of product which was contaminated by unreacted 6-chloro-nicotinicacid.

$^1$H NMR ($CDCl_3$) $\delta$=1.44 (s, 9H), $\delta$=2.37–2.56 (broad s, 7H) $\delta$=2.56–2.81 (broad s, 1H) $\delta$=2.40 (m, 1H), $\delta$=2.70 (m, 1H), $\delta$=8.45 (m, 1H), MS (ES+)=651.4 ($2M^-$), 326.4 and 328.4 (M+H).

4) Diethyl-pyridyl borane

This reagent was obtained via a modified procedure described in *Chem. Pharm. Bull.* (1985), 33 (11), p.4755

What is claimed is:

1. A compound of the formula I

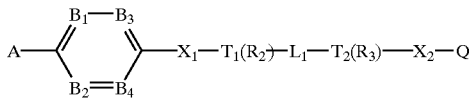

wherein:

A is an optionally substituted 5- or 6-membered monocyclic aromatic ring consisting of 1, 2 or 3 ring heteroatoms selected from oxygen, nitrogen and sulphur atoms; one of $B_1$, $B_2$, $B_3$ and $B_4$ is nitrogen and the remainder of $B_1$, $B_2$, $B_3$ and $B_4$ are CH, and wherein the ring formed from $B_1$, $B_2$, $B_3$ and $B_4$ may optionally be substituted by one or two substituents selected from hydroxy, carboxy, (1–4C) alkoxycarbonyl or one of the following:

-$(CH_2)_n$-R, -$(CH_2)_n$-$NRR_1$, —CO—R, —CO—$NRR_1$, -$(CH_2)_n$-CO—R and -$(CH_2)_n$-CO—$NRR_1$;

wherein n is 1 or 2;

R and $R_1$ are independently selected from hydrogen, (1–4C)alkyl, (2–4C)alkenyl, (2–4C)alkynyl, hydroxy (1–4C)alkyl, carboxy(1–4C)alkyl and (1–4C) alkoxycarbonyl-(1–4C)alkyl, or R and $R_1$ may together form a 5- or 6-membered optionally substituted heterocyclic ring which may include in addition to the nitrogen atom to which R and $R_1$ are attached one or two additional heteroatoms selected from nitrogen, oxygen and sulphur;

$T_1$ is CH or N;

$T_2$ is CH or N;

with the proviso that at least one of $T_1$ and $T_2$ is N;

$X_1$ is SO, $SO_2$, $C(R_4)_2$ or CO when $T_1$ is CH or N; or in addition $X_1$ is O or S when $T_1$ is CH; and wherein each $R_4$ is independently hydrogen or (1–4C)alkyl;

$L_1$ is (1–4C)alkylene or (1–3C)alkylenecarbonyl;

$R_2$ is hydrogen or (1–4C)alkyl;

$R_3$ is hydrogen or (1–4C)alkyl;

or $R_2$ and $R_3$ are joined to form a $C_{1-4}$alkylene or —$CH_2CO$— group; wherein the ring formed by $T_1$, $R_2$, $R_3$, $T_2$ and $L_1$ is optionally substituted;

$X_2$ is $SO_2$; and

Q is phenyl, naphthyl, phenyl(1–4C)alkyl, phenyl(2–C) alkenyl, phenyl(2–4C)alkynyl or a heterocyclic moiety containing up to 4 ring heteroatoms selected from nitrogen, oxygen and sulphur and Q is optionally substituted;

or a pharmaceutically acceptable salt thereof.

2. The compound of formula I as claimed in claim 1 wherein Q is optionally substituted by one, two or three substituents selected from halo, trifluromethyl, trifluoromethoxy, cyano, hydroxy, amino, nitro, trifluoromethanesulphonyl, carboxy, carbamoyl, (1–4C) alkyl, (2–4C)alkenyl, (2–4C)alkynyl, (1–4C)alkoxy, (2–4C) alkenyloxy, (2–4C)alkynyloxy, (1–4C)alkylthio, (1–4C) alkylsulphinyl, (1–4C)alkylsulphonyl, (1–4C)alkylamino, di-(1–4C)alkylamino, (1–4C)alkoxycarbonyl, N-(1–4C) alkylcarbamoyl, N,N-di-(1–4C)alkylcarbamoyl, (2–4C) alkanoyl, (2–4C)alkanoylamino, hydroxy-(1–4C)alkyl, (1–4C)alkoxy-(1–4)alkyl, carboxy-(1–4C)alkyl, (1–4C) alkoxycarbonyl-(1–4C)alkyl, carbamoyl-(-4C)alkyl, N-(1–4C)alkylcarbamoyl-(1–4C)alkyl, N,N-di(1–4C) alkylcarbamoyl-(1–4C)alkyl, phenyl, heteroaryl, phenoxy, phenylthio, phenylsulphinyl, phenylsulphonyl, benzyl, benzoyl, heteroaryloxy, heteroarylthio, heteroarylsulphinyl and heteroarylsulphonyl, and wherein said heteroaryl substituent or the heteroaryl group in a heteroaryl-containing substituent is a 5- or 6-membered monocyclic heteroaryl ring consisting of up to 3 heteroatoms selected from nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1, 2 or 3 substituents selected from halogeno, trifluoromethyl, cyano, hydroxy, amino, nitro, carboxy, carbamoyl, (1–4C)alkyl, (1–4C)alkoxy, (1–4C)alkylamino, di-(1–4C)alkylamino, (1–4C) alkoxycarbonyl, N-(1–4C)alkylcarbamoyl, N,N-di-(1–4C) alkylcarbamoyl and (2–4C)alkanoylamino.

3. The compound of formula I as claimed in claim 1 or claim 2 wherein a ring is formed by $T_1$, $R_2$, $R_3$, $T_2$ and $L_1$, which ring is optionally substituted by one or two substituents selected from hydroxy, oxo, carboxy, (1–4C) alkoxycarbonyl, -$(CH_2)_n$-R, -$(CH_2)_n$-$NRR_1$, —CO—R, —C—$NRR_1$, -$(CH_2)_n$-CO—R, and -$(CH_2)_n$-$CONR_1$;

wherein n is 1 or 2;

R and $R_1$ are independently selected from hydrogen, (1–4C) alkyl, (2–4C)alkenyl, (2–4C)alkynyl, hydroxyl(1–4C) alkyl, carboxyl(1–4C)alkyl and (1–4C)alkoxycarbonyl (1–4C)alkyl, or —$NRR_1$ forms a 5- or 6-membered optionally substituted heterocyclic ring which may include, in addition to the nitrogen atom to which R and $R_1$ are attached, 1 or 2 additional selected from nitrogen, oxygen and sulphur.

4. The compound of formula I as claimed in claim 1 or claim 2 wherein $X_1$ is CO.

5. The pharmaceutical composition comprising a compound of formula I, as defined in claim 1 or claim 2, together with a pharmaceutically acceptable diluent or carrier.

* * * * *

UNITED STATES PATENT AND TRADEMARK OFFICE
CERTIFICATE OF CORRECTION

PATENT NO.  : 6,458,793 B1
DATED       : October 1, 2003
INVENTOR(S) : Warner et al.

It is certified that error appears in the above-identified patent and that said Letters Patent is hereby corrected as shown below:

Column 20,
Line 44, after "additional" insert -- heteroatoms --.

Signed and Sealed this

Twelfth Day of August, 2003

JAMES E. ROGAN
*Director of the United States Patent and Trademark Office*